United States Patent
Baney et al.

(10) Patent No.: US 6,882,428 B2
(45) Date of Patent: Apr. 19, 2005

(54) OPTICAL ANALYZER AND METHOD FOR REDUCING RELATIVE INTENSITY NOISE IN INTERFEROMETRIC OPTICAL MEASUREMENTS USING A CONTINUOUSLY TUNABLE LASER

(75) Inventors: Douglas M. Baney, Los Altos, CA (US); Gregory D. VanWiggeren, Los Gatos, CA (US); Ali Motamedi, Cambridge, MA (US)

(73) Assignee: Agilent Technologies, Inc., Palo Alto, CA (US)

( * ) Notice: Subject to any disclaimer, the term of this patent is extended or adjusted under 35 U.S.C. 154(b) by 163 days.

(21) Appl. No.: 10/305,597

(22) Filed: Nov. 27, 2002

(65) Prior Publication Data

US 2003/0112442 A1 Jun. 19, 2003

Related U.S. Application Data

(63) Continuation-in-part of application No. 09/940,741, filed on Aug. 28, 2001, now Pat. No. 6,606,158.

(51) Int. Cl.[7] .............................. G01B 9/02; G01N 21/00
(52) U.S. Cl. ........................ 356/477; 356/491; 356/731
(58) Field of Search .............................. 356/477, 491, 356/73.1; 250/227.17, 277.19, 227.27

(56) References Cited

U.S. PATENT DOCUMENTS

| | | | |
|---|---|---|---|
| 6,606,158 B1 * | 8/2003 | Rosenfeldt et al. | 356/477 |
| 6,750,973 B1 * | 6/2004 | Tan et al. | 356/477 |
| 2002/0113972 A1 | 8/2002 | Rosenfeldt et al. | |
| 2003/0112442 A1 | 6/2003 | Baney et al. | |
| 2003/0174337 A1 * | 9/2003 | VanWiggeren | 356/477 |
| 2003/0223073 A1 * | 12/2003 | VanWiggeren et al. | 356/477 |

FOREIGN PATENT DOCUMENTS

| | | |
|---|---|---|
| EP | 0280075 A2 | 8/1988 |
| EP | 1113250 A1 | 11/2000 |
| EP | 1130814 A2 | 5/2001 |
| EP | 1207377 A2 | 11/2001 |

OTHER PUBLICATIONS

Gregory D. VanWiggeren, Ali R. Motamedi, Bogdan Szafraniec, Rod S. Tucker and Douglas M. Baney, "Single–Scan Polarization–Resolved Heterodyne Optical Network Analyzer", published in OFC 2002 Technical Digest, Session WK2.

Copy of the European Search Report Dated: Nov. 10, 2004.

* cited by examiner

*Primary Examiner*—Gregory J. Toatley, Jr.
*Assistant Examiner*—Patrick Connolly

(57) ABSTRACT

A heterodyne optical network analyzer and method for device characterization reduces the effect of relative intensity noise (RIN) in interferometric optical measurements by subtracting the measured intensities of first and second interference signals derived from an optical interferometer. The first and second interference signals are produced by combining a first lightwave transmitted to an optical device being characterized with a second lightwave, which is a delayed version of the first lightwave. The first and second lightwaves are derived by splitting an input lightwave having a continuously swept optical frequency generated by a light source, such as a continuously tunable laser.

28 Claims, 5 Drawing Sheets

OPTICAL ANALYZER AND METHOD FOR REDUCING RELATIVE INTENSITY NOISE IN INTERFEROMETRIC OPTICAL MEASUREMENTS USING A CONTINUOUSLY TUNABLE LASER

CROSS REFERENCE TO RELATED APPLICATION

The present application is a continuation-in-part of U.S. patent application Ser. No. 09/940,741 filed Aug. 28, 2001, now U.S. Pat. No. 6,606,158.

FIELD OF THE INVENTION

The invention relates generally to optical network analysis, and more particularly to an optical analyzer and method for determining optical properties of an optical device using interferometric optical measurements.

BACKGROUND OF THE INVENTION

Heterodyne optical network analysis is becoming an important tool for determining optical properties of optical devices, such as fiber Bragg gratings and optical fibers. Optical properties determined using a heterodyne optical network analyzer may include reflectivity, transmissivity, group delay, differential group delay and polarization dependent loss. A heterodyne optical network analyzer determines the optical properties of a device-under-test (DUT) from the amplitude and phase of interference signals. The interference signals are obtained by detecting the interference of two combined lightwaves. Typically, one of these lightwaves has been reflected off or transmitted through the DUT, and the other lightwave is a time-delayed version of the lightwave that was incident on the DUT.

A simple heterodyne optical network analyzer in a Mach-Zehnder interferometric configuration includes a tunable laser, an optical splitter, a DUT, an optical coupler, a detector, and an evaluation device. The tunable laser, which can be continuously tuned across an optical frequency range, generates an input lightwave having an optical frequency that sweeps over a predefined frequency range free of longitudinal mode hops. Longitudinal mode hops are laser frequency hops that can cause an abrupt change in the phase of an interferometric detection waveform, causing loss of DUT phase response information. The input lightwave is transmitted to the optical splitter, where it is split into two lightwaves that propagate along different optical paths. The lightwave following the first optical path travels through the DUT to the optical coupler, whereas the lightwave following the second optical path travels directly to the optical coupler. However, the second optical path has a different length than the first optical path. Thus, the lightwave on the second optical path experiences a positive or negative time delay relative to the lightwave on the first optical path. At the optical coupler, the lightwaves from the first and second optical paths are combined. The combined lightwaves are transmitted to the detector, where they interfere. To satisfy the Nyquist limit, the intensity of the interference signal is measured with a sampling rate at least twice the frequency of the interference signal. The measured intensity of the interference signal is then analyzed by the evaluation device to determine one or more optical properties of the DUT. As an example, the transmissivity of the DUT as a function of wavelength can be determined from the amplitude of the interference signal, which is proportional to the amplitude of the lightwave on the first optical path that traveled through the DUT. As another example, the group delay of the DUT can be determined by differentiating the phase of the interference signal with respect to frequency.

A concern with the described conventional heterodyne optical network analyzer is that under certain situations intensity noise may be incident on the optical detector along with the desired interference signal. The intensity noise can significantly degrade the measurements being made by the analyzer to determine the desired optical properties of a DUT. Often, intensity noise is quantified as relative intensity noise, or RIN. RIN is defined herein as the power spectral density of intensity or photocurrent fluctuations integrated over a predefined electronic bandwidth divided by the average optical power or photocurrent squared. It is understood that reducing intensity noise or detected intensity noise is equivalent to reducing RIN since both depend on the intensity noise. A typical laser used in a heterodyne optical network analyzer will have fluctuations in its output intensity due to a variety of reasons such as the well-known signal-spontaneous beat noise and multi-path interference (MPI). See Derickson, *Fiber Optic Test and Measurement*, Chapter 5 and Chapter 13, Prentice Hall (1998). These fluctuations can have a very broad spectral content, which can interfere with the measurements being made by the heterodyne optical network analyzer. Additionally, the DUT itself can generate intensity noise, which can mask or obscure the desired interferometric measurements.

In view of this concern, what is needed is a heterodyne optical network analyzer and method for reducing the effect of relative intensity noise in interferometric optical measurements for device characterization.

SUMMARY OF THE INVENTION

A heterodyne optical network analyzer and method for device characterization reduces the effect of relative intensity noise (RIN) in interferometric optical measurements by subtracting the measured intensities of first and second interference signals derived from an optical interferometer. The first and second interference signals are produced by combining a first lightwave transmitted to an optical device being characterized with a second lightwave, which is a delayed version of the first lightwave. The first and second lightwaves are derived by splitting an input lightwave having a continuously swept optical frequency generated by a light source, such as a continuously tunable laser. The reducing of the RIN effect results in a more accurate interferometric device characterization of the optical device.

In accordance with the invention, a heterodyne optical network analyzer includes a light source, an optical interferometer with an optical device and a subtraction unit. The light source is configured to generate an input lightwave having a continuously swept optical frequency. The optical interferometer is configured to produce first and second interference signals, which contain noise components, using a first lightwave from the optical device and a second lightwave. The first and second lightwaves are derived from the input lightwave. The subtraction unit is configured to subtract the intensities of the first and second interference signals to derive a differential signal with a reduced amount of noise components, which contains information related to optical properties of the optical device.

In accordance with the invention, a method of reducing the effect of RIN includes the steps of producing first and second interference signals, which contain noise components, using a first lightwave from an optical device and a second lightwave, and subtracting the intensities of the first and second interference signals with a reduced amount of noise components, which contains information related to optical properties of the optical device. The first and second lightwaves have continuously swept optical frequencies.

Other aspects and advantages of the present invention will become apparent from the following detailed description, taken in conjunction with the accompanying drawings, illustrated by way of example of the principles of the invention.

DETAILED DESCRIPTION

Figure 1:
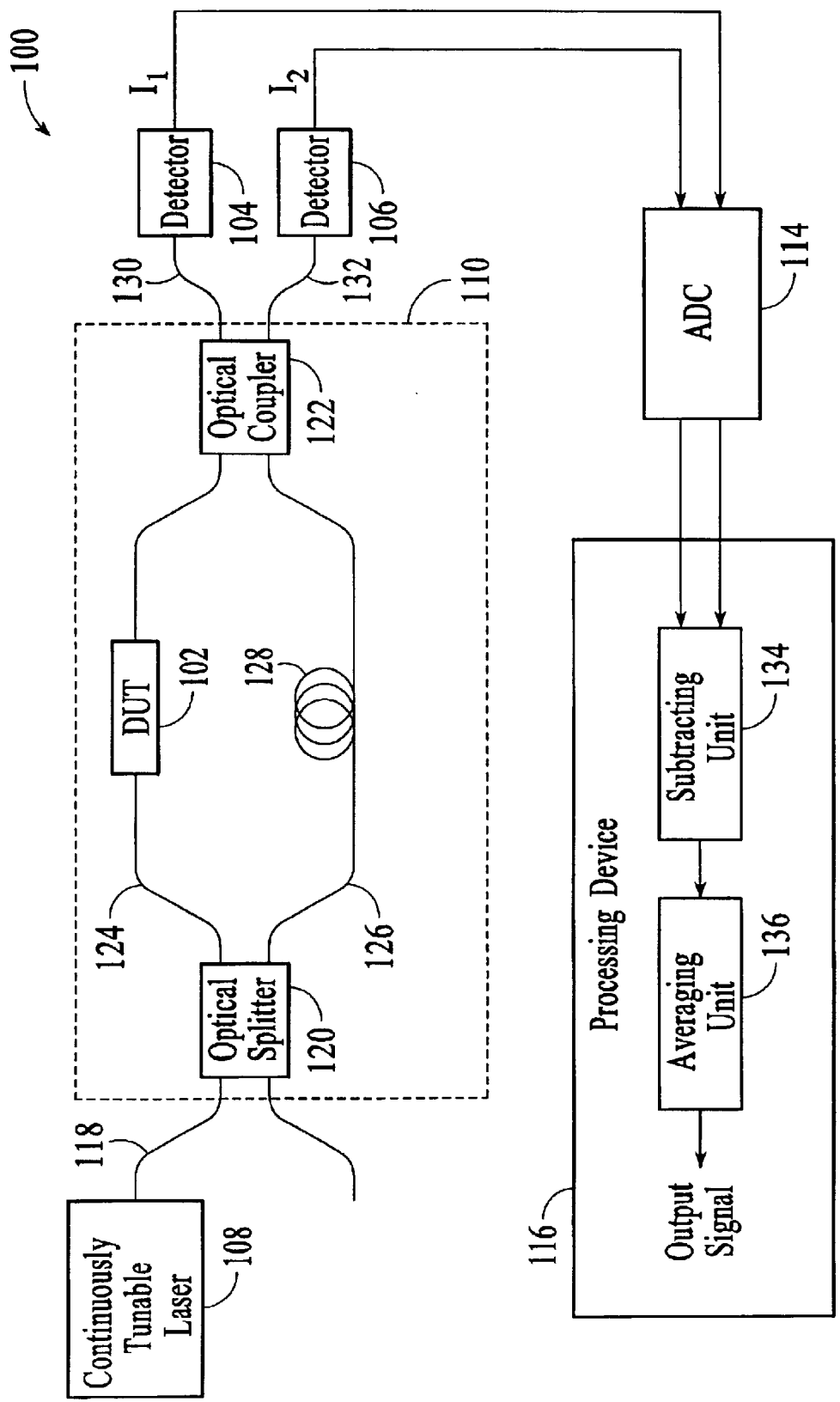
FIG. 1 is a diagram of a heterodyne optical network analyzer of an embodiment in accordance with the present invention.

With reference to FIG. 1, a heterodyne optical network analyzer 100 of an embodiment in accordance with the invention is shown. The heterodyne optical network analyzer operates to determine the optical properties of a device-under-test (DUT) 102 by measuring the intensity of an interference signal, which is produced from a combined signal of a lightwave transmitted through the DUT and a time-delayed version of the same lightwave. However, unlike a conventional heterodyne optical network analyzer, the heterodyne optical network analyzer 100 utilizes a pair of balanced detectors 104 and 106 to reduce the effect of relative intensity noise (RIN) in the interferometric optical measurements made by the analyzer. As described in more detail below, the balanced detectors are used to significantly remove RIN components in the interference signal, which results in better characterization of the DUT.

The heterodyne optical network analyzer 100 includes a light source 108, an optical interferometer 110 with the DUT 102, the balanced detectors 104 and 106, an analog-to-digital converter (ADC) 114, and a processing device 116. The light source 108 is capable of tuning the light output frequency over a frequency range without longitudinal mode hops. Thus, the light source can generate a lightwave having an optical frequency that continuously sweeps over a predefined frequency range. In this embodiment, the light source is a continuously tunable laser, and thus, the light source is illustrated and described below as a continuously tunable laser. However, the light source can be any device that can generate a lightwave having a continuously swept optical frequency. The lightwave from the continuously tunable laser is transmitted to the optical interferometer 110 along an optical path 118.

In FIG. 1, the optical interferometer 110 of the heterodyne optical network analyzer 100 is shown to be arranged in a simple Mach-Zehnder interferometric configuration to analyze signals transmitted through the DUT 102. However, the optical interferometer 110 can be arranged in any interferometric configuration. As an example, the optical interferometer 110 can be arranged in a Michelson interferometric configuration to analyze signals reflected off the DUT.

The optical interferometer 110 shown in FIG. 1 includes an optical splitter 120, the DUT 102, and an optical coupler 122. The optical splitter 120 is configured to split the lightwave from the continuously tunable laser 108 into two lightwaves. One of the split lightwaves is transmitted to the optical coupler 122 through the DUT 102 along an optical path 124. The other split lightwave is transmitted directly to the optical coupler along an optical path 126. The length of the optical path 126 is different than the length of the optical path 124, as indicated by loops 128 on the optical path 126. Thus, the lightwave on the optical path 124 or 126 experiences a time-delay of $_\tau$, which is dependent on the relative lengths of the optical paths 124 and 126, with respect to the other lightwave. The optical coupler 122 is configured to combine the lightwaves propagating along the paths 124 and 126 to produce combined signals on paths 130 and 132. The combined signals on paths 130 and 132 are transmitted to the detectors 104 and 106, where the combined signals interfere to produce interference signals. Due to the property of the optical coupler 122, the interference signal detected by the detector 106 is phase shifted by 180 degrees in comparison with the interference signal detected by the detector 104.

The detectors 104 and 106 of the optical network analyzer 100 are configured to generate current in response to received optical signal. Thus, the interference signal at the detector 104 is converted to a photo-generated current $I_1$ by the detector 104. Similarly, the interference signal at the detector 106 is converted to a photo-generated current $I_2$. The amount of current generated by each detector is proportional to the intensity of the interference signal at that detector. Thus, the current $I_1$ generated by the detector 104 corresponds to the intensity of light propagating along the optical path 130. Similarly, the current $I_2$ generated by the detector 106 corresponds to the intensity of light propagating along the optical path 132. The generated currents $I_1$ and $I_2$ are transmitted to the ADC 114, which converts the currents into digitized signals for digital processing.

Figure 2:
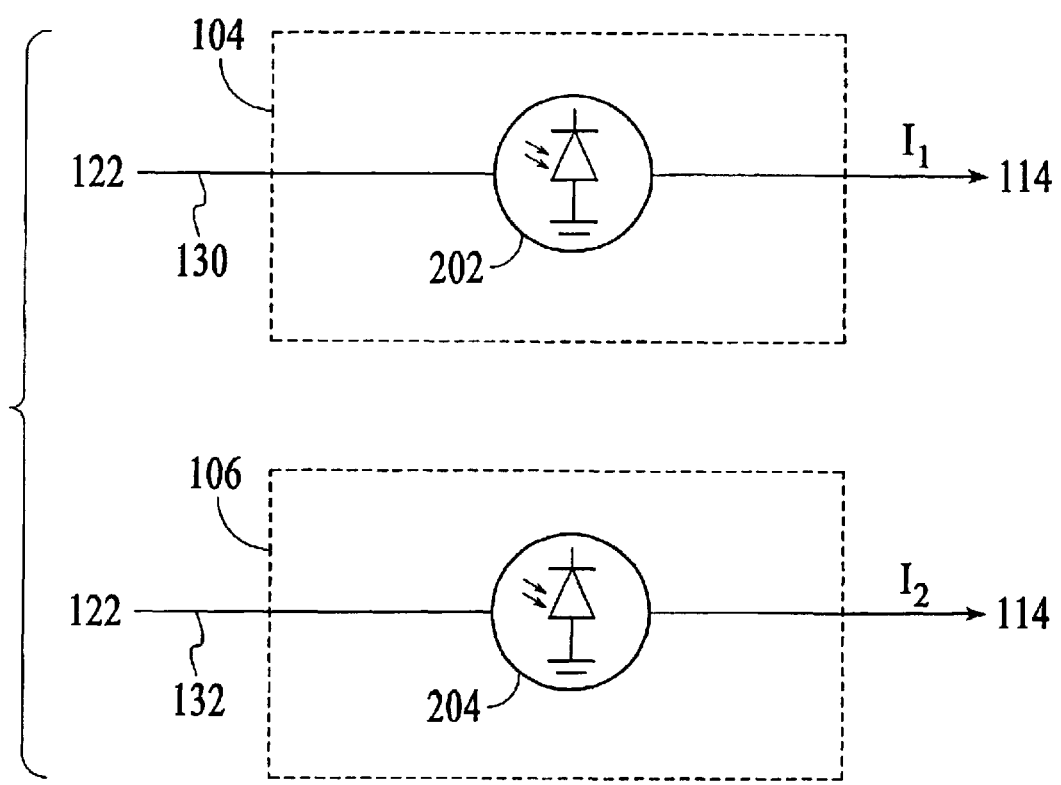
FIG. 2 illustrates detectors of the heterodyne optical network analyzer of FIG. 1.

As an example, each of the detectors 104 and 106 may include a single photosensitive device, such as a photodiode, to measure the intensity of the respective interference signal at the detectors. As illustrated in FIG. 2, the detector 104 may include a photodiode 202, and the detector 106 may include a photodiode 204. The photodiode 202 converts the interference signal at the detector 104 into the current $I_1$. Similarly, the photodiode 204 converts the interference signal at the detector 106 into the current $I_2$. The generated currents $I_1$ and $I_2$ are transmitted to the ADC 114.

The interference signal measured by the detector 104, which is typically used in conventional heterodyne optical network analyzers for interferometric optical measurements of the DUT 102, contains noise components that are attributable to RIN. However, due to the characteristics of the two interference signals measured by the detectors 104 and 106, as described in more detail below, some of the noise components in the interference signal measured by the detector 104 can be reduced by subtracting from it the interference signal measured at the detector 106. Several such measurements can then be averaged to further reduce the noise components in the interference signal measured by the detector 104. The processing device 116 performs these operations to remove RIN components from the interference signal measured by the detector 104. This allows a desired interference signal to be obtained, which can then be used to determine the optical properties of the DUT.

As illustrated in FIG. 1, the processing device 116 of the heterodyne optical network analyzer 100 includes a subtracting unit 134 and an averaging unit 136. The subtracting unit 134 operates to subtract the measured current $I_2$ from the measured current $I_1$ to derive a differential signal. The averaging unit 136 operates to average either differential signals made over several measurements or optical parameters derived from the differential signals, such as amplitude and phase, to further reduce the noise components. The averaging unit produces an output signal, which is the desired signal that can be used to determine the optical properties of the DUT. The analyzing techniques to determine the optical properties using the output signal are well known, and thus, are not described herein. The subtracting and averaging units of the processing device represent functional blocks. Thus, these components may or may not be physical components. The subtracting and averaging units may be implemented in any combination of hardware, software and/or firmware.

Mathematical basis for reducing RIN in heterodyne optical network analysis in accordance with the invention is now described with reference to FIG. 1. At the optical coupler 122, let the lightwave that traveled on the optical path 124 through the DUT 102 be defined as: $E_{DUT}(t) = E_D(t)e^{jwt}$, where $w(t) = \int \omega(t)dt$ and $\omega$ is the optical frequency of the original lightwave output from the tunable laser 108. Similarly, let the lightwave that traveled on the optical path 126 be defined as: $E_{REF}(t) = E_R(t)e^{jw(t+\tau)[t+\tau]}$, where $\tau$ is the delay due to the difference in lengths of the optical paths 124 and 126. The intensity of the interference signal measured at the detector 104 can then be calculated according to the following formula.

$$I_1(t) = |E_{DUT} + E_{REF}|^2 \quad (1.1)$$
$$= E_D(t)^2 + E_R^2 + 2E_D(t)E_R\cos(\omega(t+\tau/2)\tau)$$

Equation (1.1) can be used to determine the optical properties of the DUT 102. As an example, the amplitude of the interference term $2E_D(t)E_R\cos(\omega(t+\tau/2)\tau)$ in the equation (1.1) is proportional to the amplitude of the lightwave transmitted through the DUT, $E_D$. This relationship can then be used to determine the transmissivity of the DUT as a function of wavelength. As another example, the phase of the interference signal as defined by equation (1.1) can be differentiated with respect to the optical frequency, $\omega$, in order to determine the group delay of the DUT.

However, the analysis of the interference signal at the detector 104 becomes more complicated when RIN is introduced. The lightwave transmitted through the DUT 102 can be defined as: $E_{DUT}(t) = E_D(t)e^{jwt} + \Re_D(t)$, where $\Re_D(t)$ represents small complex amplitude fluctuations that give rise to RIN on that lightwave. Similarly, the time-delayed lightwave on the optical path 126 can be defined as: $E_{REF}(t) = E_R e^{jw(t+\tau)[t+\tau]} + \Re(t)$. Using these definitions, the intensity of the interference signal at the detector 104 must be rewritten as:

$$I_1(t) = |E_{DUT} + E_{REF}|^2 \quad (1.2)$$
$$= E_D(t)^2 + E_R^2 + 2E_D(t)E_R\cos(\omega(t-\tau/2)\tau) +$$
$$\Re_D^2(t) + \Re_R^2(t) + 2\text{Re}\{\Re_D(t)E_D e^{-jwt} + \Re_R(t)E_R e^{-jw(1+\tau)[1+\tau]} +$$
$$\Re_D(t)\Re_R^*(t) + \Re_R(t)E_D e^{-jwt} + \Re_D(t)E_R e^{-jw(1+\tau)[1+\tau]}\}.$$

In conventional heterodyne optical network analyzers, the intensity defined by the equation (1.2) is used to determine the optical properties of the DUT 102. If the RIN terms in the equation 1.2, i.e., $\Re_D^2(t)$, $\Re^{R2}(t)$ and 2 Re{ }, are significant, then the measurements made by the conventional heterodyne optical network analyzers will not be accurate.

As stated above, the heterodyne optical network analyzer 100 in accordance with the invention reduces the RIN components by subtracting the interference signal at the detector 106 from the interference signal at the detector 104. In this embodiment, the measured intensity $I_2$ of the interference signal at the detector 106 is subtracted from the measured intensity $I_1$ of the interference signal at the detector 104. As described mathematically in detail below, subtracting the measured intensity $I_2$ from the measured intensity $I_1$ can significantly reduce RIN components.

Laser RIN is typically due to three primary components, which are shot noise, signal-spontaneous beat noise and multi-path interference noise. Shot noise is caused by quantum-mechanical uncertainties in the arrival times of photons at a detector. Signal-spontaneous beat noise is caused by intensity fluctuations due to interference of signal light with amplified spontaneous emission (ASE) noise. Multi-path interference noise is caused by interferometric conversion of laser phase noise into intensity noise due to the presence of optical reflections. The technique employed by the heterodyne optical network analyzer 100 does not reduce RIN due to shot noise. However, the technique does reduce RIN due to signal-spontaneous beat noise and multi-path interference. Signal-spontaneous beat noise, for example, becomes especially important for measurements involving active devices, such as optical amplifiers.

As stated above, signal-spontaneous beat noise is caused by intensity fluctuations due to interference of signal light with ASE noise. The source of the ASE noise can be modeled by assuming that $\Re_D(t) = R_D(t)e^{j\{wt+\phi_1\}}$ and $\Re_R(t) = R_R(t)e^{j\{w(t+\tau)[t+\tau]+\phi_2\}}$, where $\phi_{1,2}(t)$ represent random phase fluctuations resulting from the statistical fluctuations of the ASE noise. Naturally, these ASE noise sources have an optical frequency similar to the signal lightwaves. Using the assumption, equation (1.2) can now be written as:

$$I_1(t) = |E_{DUT} + E_{REF}|^2 \quad (1.3)$$
$$= E_D(t)^2 + E_R^2 + 2E_D(t)E_R\cos(\omega(t+\tau/2)\tau) +$$
$$R_D^2(t) + R_R^2(t) + 2\text{Re}\{R_D(t)E_D(t)e^{+j\varphi_1(t)} + R_R(t)E_R e^{+j\varphi_2(t)} +$$
$$R_D(t)R_R(t)e^{-j[\omega(t+\tau/2)\tau - \varphi_1(t) + \varphi_2(t)]} + R_R(t)E_D(t)e^{j[\omega(t+\tau/2)\tau + \varphi_2(t)]} +$$
$$R_D(t)E_R e^{-j[\omega(t+\tau/2)\tau - \varphi_1(t)]}\}$$

Assuming that the intensity measured at the detector 104 is defined by equation (1.3), the intensity measured at the other detector 106 is defined by the following equation.

$$I_2(t) = |E_{DUT} + E_{REF}|^2 \quad (1.4)$$
$$= E_D(t)^2 + E_R^2 - 2E_D(t)E_R\cos(\omega(t+\tau/2)\tau) +$$
$$R_D^2(t) + R_R^2(t) + 2\text{Re}\{R_D(t)E_D e^{+j\varphi_1(t)} + R_R(t)E_R e^{+j\varphi_2(t)} -$$
$$R_D(t)R_R(t)e^{-j[\omega(t+\tau/2)\tau - \varphi_1(t) + \varphi_2(t)]} - R_R(t)E_D(t)e^{j[\omega(t+\tau/2)\tau + \varphi_2(t)]} -$$
$$R_D(t)E_R e^{-j[\omega(t+\tau/2)\tau - \varphi_1(t)]}\}$$

Subtracting the two intensities, $I_1$ and $I_2$, results in the elimination of many RIN terms, as evident in the following equation.

$$I_1(t) - I_2(t) = 4E_D(t)E_R\cos(\omega(t+\tau/2)\tau) + \qquad (1.5)$$

$$4R_R(t)E_D(t)\cos(\omega(t+\tau/2)t + \varphi_2(t)) +$$

$$4R_D(t)E_R\cos(\omega(t+\tau/2)\tau + \varphi_1(t)) +$$

$$4R_D(t)R_R(t)\cos(\omega(t+\tau/2) - \varphi_1(t) + \varphi_2(t))$$

The first term of equation (1.5) is the desired signal. The remaining terms are noise terms. The last noise term is likely to be small relative to all of the other terms. The three noise terms can be reduced or eliminated by averaging over several measurements. For RIN caused by ASE, averaging should cause the noise terms to approach an average value of zero because of the stochastic nature of the phases, $\phi_{1,2}(t)$. This allows isolation of the signal of interest, $4E_D(t)E_R \cos(\omega)(t+\tau/2)\tau)$.

The same analysis can be performed for multi-path interference noise, which would produce results that are nearly the same. However, there is one important distinction. In the analysis for signal-spontaneous beat noise, the phases, $\phi_{1,2}(t)$, varied randomly due to ASE noise in the tunable laser 108. For multi-path interference, however, the phases represent the effect of the different path taken by the light that causes the RIN. The phases, $\phi_{1,2}(t)$, will increase linearly at a rate proportional to the path mismatch of the multi-path interference. Thus, the variation is deterministic and systematic. Consequently, averaging over several measurements will not remove these three remaining noise terms. However, the three noise terms in equation (1.5) may oscillate at a different frequency than the term of interest (the first term). More specifically, if the path delay of the multi-path interference is sufficiently large, i.e., the slope of $\phi_{1,2}(t)$ is sufficiently large, then a bandpass filter applied to the frequency of the first term can eliminate the effect of the three remaining terms.

Figure 3:
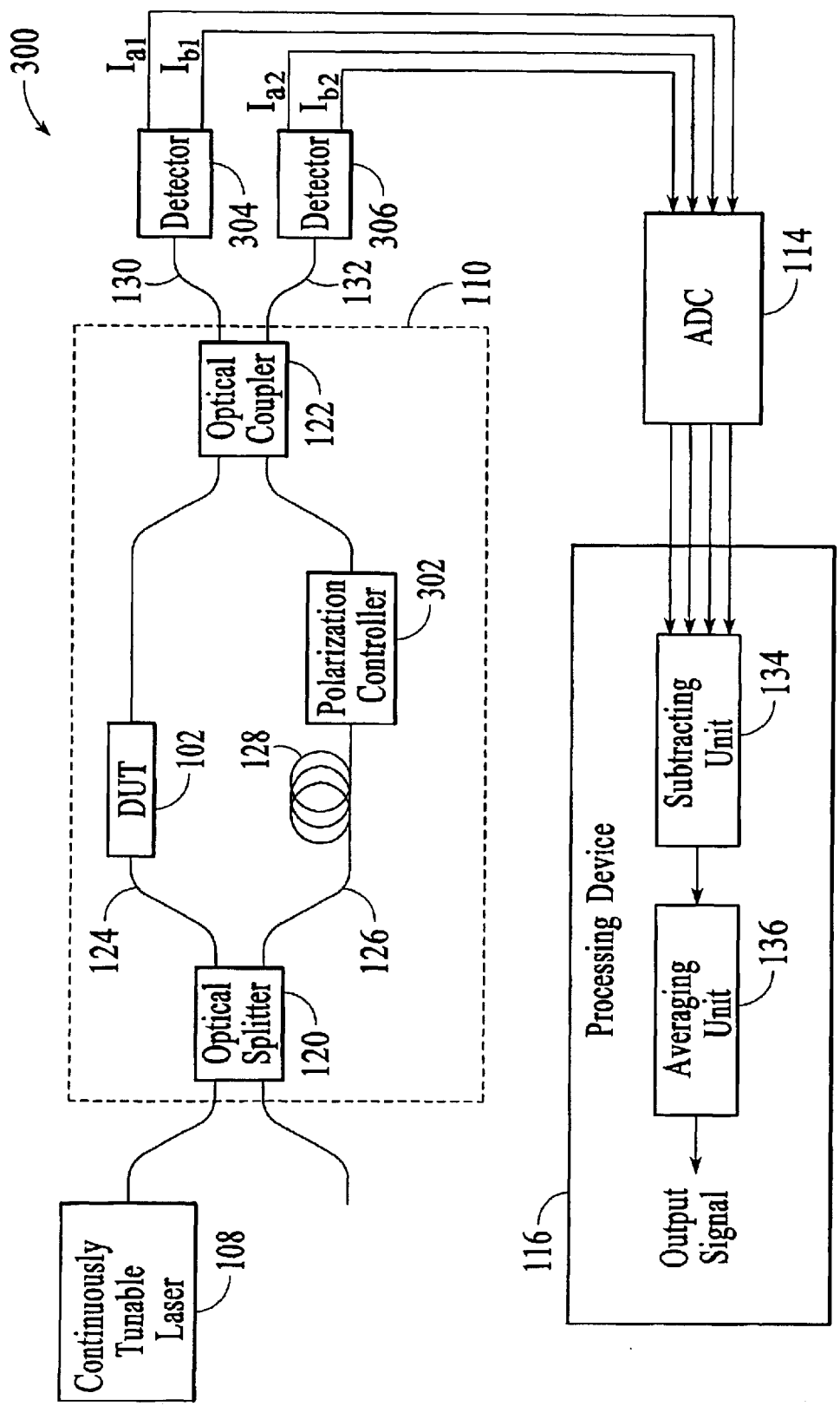
FIG. 3 is a diagram of a heterodyne optical network analyzer of an embodiment in accordance with the present invention.

Turning now to FIG. 3, a heterodyne optical network analyzer 300 of an embodiment in accordance with the invention is shown. Typically, interference between two lightwaves occurs only when the lightwaves possess the same polarization. Thus, the magnitude of the detected interference signal can vary depending on the relative polarizations of the interfering lightwaves. However, the heterodyne optical network analyzer 300 is configured so that the magnitudes of the detected interference signals can be made independent of the relative polarizations of the interfering lightwaves.

In FIG. 3, the same reference numbers of FIG. 1 are used to identify those elements that are common to both embodiments. The heterodyne optical network analyzer 300 of FIG. 3 includes a polarization controller 302 on the path 126 and detectors 304 and 306, which are configured as polarization diverse receivers, so that polarization independent measurements can be made. The polarization controller 302 is configured to adjust the polarization of the lightwave propagating along the path 126 so that the power of this lightwave is divided evenly at the detectors 304 and 306. As an example, the polarization controller may be a fiber optic paddle-type controller. Adjusting the polarization of the lightwave in the path 126 so that its power is split perfectly evenly is difficult. Consequently, a calibration procedure to account for imperfect alignment of this lightwave would typically be used.

Figure 4:
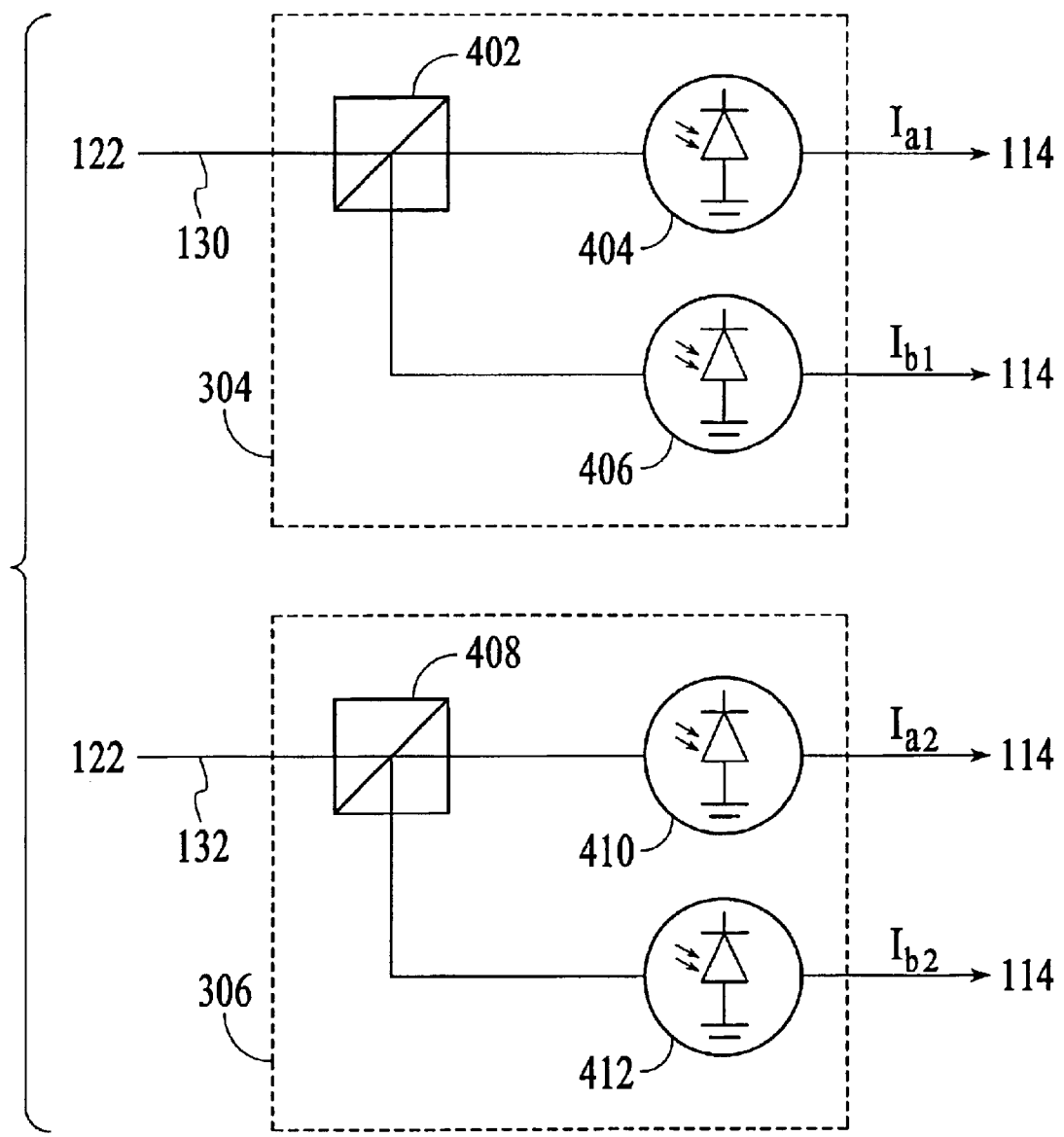
FIG. 4 illustrates polarization diverse detectors of the heterodyne optical network analyzer of FIG. 3.

As illustrated in FIG. 4, the detector 304 includes a polarization beam splitter 402 and two photosensitive devices 404 and 406. Similarly, the detector 306 includes a polarization beam splitter 408 and two photosensitive devices 410 and 412. The photosensitive devices 404, 406, 410 and 412 may be photodiodes, as shown in FIG. 4. The polarization beam splitters 402 and 408 are configured to divide the combined signals propagating along the respective paths 130 and 132 into orthogonally polarized components. At the detector 304, the orthogonally polarized components are transmitted to the photodiode 404 or 406, depending on their polarizations. Thus, components having the same polarization interfere on the respective photodiode. The photodiode 404 converts the interference signal at the photodiode 404 into current $I_{a1}$, while the photodiode 406 converts the interference signal at the photodiode 406 into current $I_{b1}$. Similarly, at the detector 306, the orthogonally polarized components are transmitted to the photodiode 410 or 412, depending on their polarizations. The photodiode 410 converts the interference signal at the photodiode 410 into current $I_{a2}$, while the photodiode 412 converts the interference signal at the photodiode 412 into current $I_{b2}$. The four generated currents $I_{a1}$, $I_{b1}$, $I_{a2}$ and $I_{b2}$ are transmitted to the processing device 116 via the ADC 114 to make polarization diverse measurement. For example, in a situation in which the polarization of the lightwave from the path 124 is the same on both polarization diverse detectors 304 and 306, the currents $I_{a1}$ and $I_{b1}$ are subtracted from the corresponding currents, $I_{a2}$ and $I_{b2}$, obtained from detector 106 to derive difference signals, $I_{a1-a2}$ and $I_{b1-b2}$, which have reduced RIN. If the polarization of the lightwave from the path 124 is different as it is incident on the polarizing beam splitters of detectors 104 and 106, a further calibration must be applied to obtain appropriate difference signals. These difference signals can then be used to determine various optical properties of the DUT 102. For example, the reflectance or transmittance of the DUT can be determined since the reflectance or transmittance is proportional to $\sqrt{|I_{a1-a2}|^2 + |I_{a2-b2}|^2}$, which can be computed by the subtracting unit 134 of the processing device 116.

Figure 5:
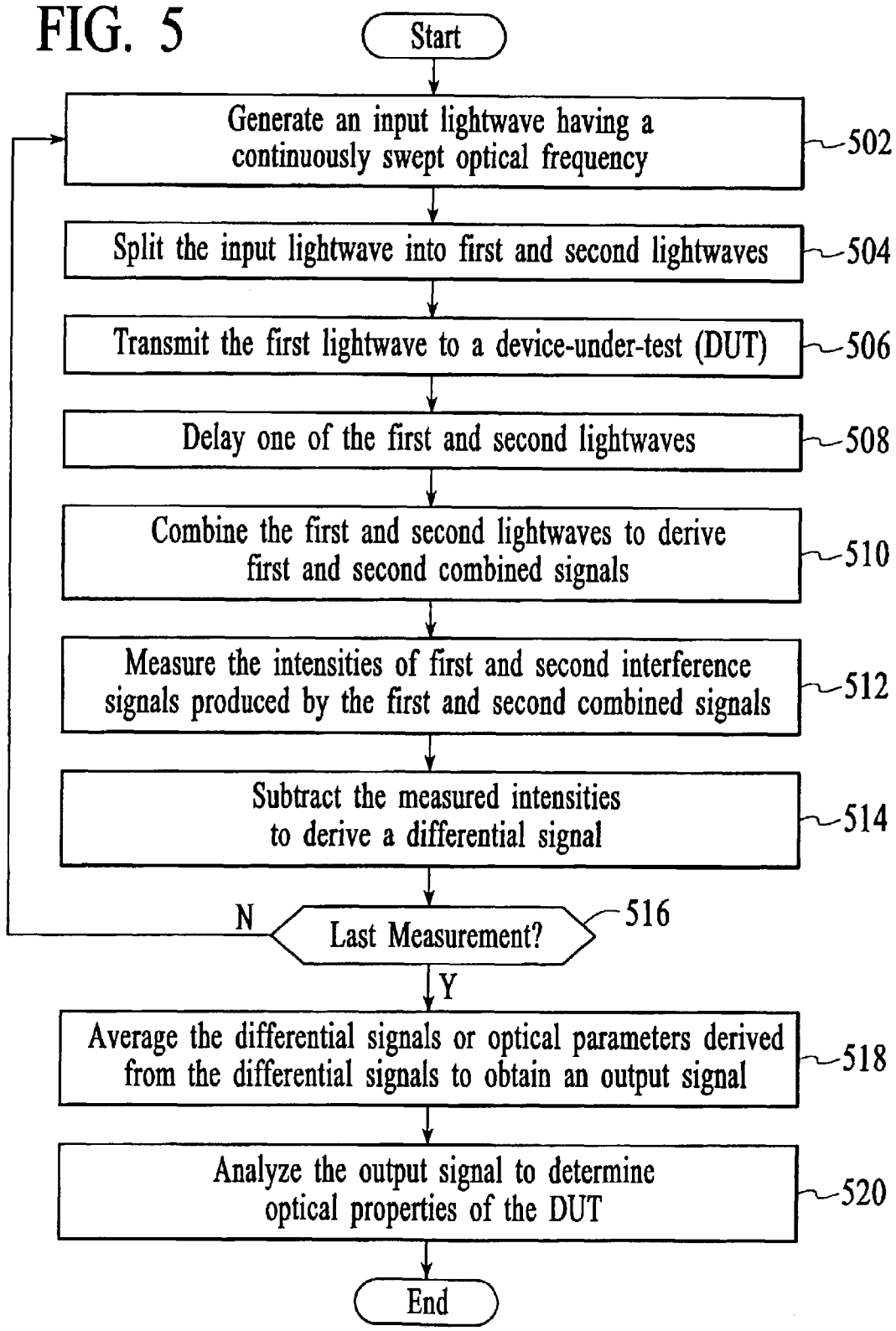
FIG. 5 is a process flow diagram of a method for reducing the effect of relative intensity noise (RIN) in interferometric optical measurements for device characterization of an embodiment in accordance with the invention.

A method for reducing the effect of RIN in interferometric optical measurements for device characterization of an embodiment in accordance with the invention is described with reference to the process flow diagram of FIG. 5. At step 502, an input lightwave having a continuously swept optical frequency is generated. Next, at step 504, the input lightwave is split into first and second lightwaves. The first lightwave is transmitted to a device-under-test (DUT), at step 506. At step 508, one of the first and second lightwaves is delayed with respect to the other lightwave. Next, at step 510, the first and second lightwaves are combined to derive first and second combined signals. At step 512, the intensities of first and second interference signals produced by the first and second combined signals are measured. Each of the first and second interference signals includes RIN components. The intensities of the first and second interference signals may be measured by generating currents using photosensitive devices, such as photodiodes, in response to the signals. The measured intensities are then subtracted to derive a differential signal, which includes a reduced amount of RIN components, at step 514.

Next, at step 516, a determination is made whether the current measurement is the last measurement to be made. If not, then the process proceeds back to step 502, and steps 502 through 516 are repeated to derive a differential signal for the next measurement. The number of measurements to be made is predetermined. If the current measurement is the last measurement to be made, then the process proceeds to step 518, where an output signal is obtained by averaging the differential signals or optical parameters, such as amplitude and phase, derived from the differential signals to further reduce RIN components. Next, at step 520, the output signal is analyzed to determine the optical properties of the DUT.

Although specific embodiments in accordance with the invention have been described and illustrated, the invention is not to be limited to the specific forms or arrangements of parts so described and illustrated. As an example, the invention can be applied to other more complex interferometric analyzer configurations, such as the single-scan interferometric analyzer described in "Single-Scan Polarization-Resolved Heterodyne Optical Network Analyzer" by VanWiggeren et al. published in the OFC 2002 Technical Digest, Session WK2, which is incorporated herein by reference. The scope of the invention is to be defined by the claims appended hereto and their equivalents.

What is claimed is:

1. A method of reducing noise in interferometric optical measurements for device characterization comprising:
   producing first and second interference signals using a first lightwave from an optical device and a second lightwave, said first and second interference signals containing noise components, said first and second lightwaves having continuously swept optical frequencies; and
   subtracting intensities of said first and second interference signals to derive a differential signal with a reduced amount of said noise components, said differential signal containing information related to optical properties of said optical device.

2. The method of claim 1 further comprising generating an input lightwave having a continuously swept optical frequency using a continuously tunable laser to provide said first and second lightwaves.

3. The method of claim 2 further comprising splitting said input lightwave to derive said first and second lightwaves.

4. The method of claim 1 further comprising measuring said intensities of said first and second interference signals using a pair of balanced detectors.

5. The method of claim 1 further comprising delaying one of said first and second lightwaves with respect to the other lightwave prior to said producing of said first and second interference signals.

6. The method of claim 1 further comprising polarization splitting at least one of said first and second combined signals, which are derived from said first and second lightwaves, into polarization components and measuring intensities of said polarization components to provide polarization diverse measurement.

7. The method of claim 1 further comprising:
   repeating said producing and said subtracting to derive a plurality of differential signals; and
   averaging said differential signals or optical parameters derived from said differential signals to obtain said information related to optical properties of said optical device.

8. The method of claim 1 wherein said second interference signal is a phase-shifted version of said first interference signal.

9. The method of claim 1 wherein said noise components include relative intensity noise components.

10. The method of claim 1 wherein said producing of said first and second interference signals includes combining said first lightwave, which is transmitted through said optical device, with said second lightwave.

11. The method of claim 1 wherein said producing of said first and second interference signals includes combining said first lightwave, which is reflected off said optical device, with said second lightwave.

12. An interferometric optical analyzer for device characterization comprising:
   a light source configured to generate an input lightwave having a continuously swept optical frequency;
   an optical interferometer with an optical device configured to produce first and second interference signals using a first lightwave from said optical device and a second lightwave, said first and second lightwaves being derived from said input lightwave, said first and second interference signals containing noise components; and
   a subtracting unit configured to subtract intensities of said first and second interference signals to derive a differential signal with a reduced amount of said noise components, said differential signal containing information related to optical properties of said optical device.

13. The optical analyzer of claim 12 wherein said light source includes a continuously tunable laser.

14. The optical analyzer of claim 12 further comprising balanced detectors configured to measure said intensities of said first and second interference signals.

15. The optical analyzer of claim 12 wherein said optical interferometer includes an optical splitter and an optical coupler, said optical splitter being configured to split said input lightwave into said first and second lightwaves, said optical coupler being configured to combine said first lightwave from said optical device with said second lightwave.

16. The optical analyzer of claim 12 wherein said optical interferometer is configured to combine said first lightwave, which has been transmitted through said optical device, with said second lightwave.

17. The optical analyzer of claim 12 wherein said optical interferometer is configured to combine said first lightwave, which has been reflected off said optical device, with said second lightwave.

18. The optical analyzer of claim 12 wherein said optical interferometer is configured to delay one of said first and second lightwaves with respect to the other lightwave.

19. The optical analyzer of claim 12 further comprising an averaging unit operatively coupled to said subtracting unit, said averaging unit being configured to average a plurality of differential signals or optical parameters derived from said differential signals to obtain said information related to said optical properties of said optical device.

20. The optical analyzer of claim 12 further comprising a detector to measure one of said intensities, said detector including a polarization beam splitter and at least two photosensitive devices, said polarization beam splitter being configured to split an incoming optical signal into polarization components, said photosensitive devices being configured to measure intensities of said polarization components to provide polarization diverse measurement.

21. The optical analyzer of claim 12 wherein said noise components contained in said first and second interference signals include relative intensity noise components.

22. The optical analyzer of claim 13 wherein said second interference signal is a phase-shifted version of said first interference signal.

23. An interferometric optical analyzer for device characterization comprising:
   a continuously tunable laser configured to generate an input lightwave having a continuously swept optical frequency;
   an optical interferometer configured to split said input lightwave into first and second lightwaves, said first lightwave being transmitted to an optical device being characterized, said optical interferometer further configured to combine said first lightwave from said optical device with said second lightwave to derive first and second combined signals;

balanced detectors configured to measure intensities of first and interference signals produced by said first and second combined signals, said first and second interference signals containing noise components; and a subtracting unit configured to subtract said intensities of said first and second interference signals to derive a differential signal with reduced amount of said noise components, said differential signal containing information related to optical properties of said optical device.

24. The optical analyzer of claim 23 wherein said optical interferometer is configured to delay one of said first and second lightwaves with respect to the other lightwave.

25. The optical analyzer of claim 23 further comprising an averaging unit operatively coupled to said subtracting unit, said averaging unit being configured to average a plurality of differential signals or optical parameters derived from said differential signals to obtain said information related to said optical properties of said optical device.

26. The optical analyzer of claim 23 wherein at least one of said balanced detectors includes a polarization beam splitter and at least two photosensitive devices, said polarization beam splitter being configured to split an incoming combined signal into polarization components, said photosensitive devices being configured to measure intensities of said polarization components to provide polarization diverse measurement.

27. The optical analyzer of claim 23 wherein said noise components contained in said first and second interference signals include relative intensity noise components.

28. The optical analyzer of claim 23 wherein said second interference signal is a phase-shifted version of said first interference signal.

* * * * *